(12) United States Patent
Gramling et al.

(10) Patent No.: US 10,315,471 B2
(45) Date of Patent: Jun. 11, 2019

(54) SENSING DEVICE WITH PROXIMITY DETECTION FOR TIRE INSPECTION

(71) Applicants: Compagnie Generale des Etablissements Michelin, Clermont-Ferrand (FR); Frank Gramling, Simpsonville, SC (US); Bradley Schober, Greer, SC (US); David Judd, Mauldin, SC (US)

(72) Inventors: Frank Gramling, Simpsonville, SC (US); Bradley Schober, Greer, SC (US); David Judd, Mauldin, SC (US)

(73) Assignee: Compagnie Generale des Etablissements Michelin, Clermont-Ferrand (FR)

( * ) Notice: Subject to any disclaimer, the term of this patent is extended or adjusted under 35 U.S.C. 154(b) by 85 days.

(21) Appl. No.: 15/567,749

(22) PCT Filed: Mar. 24, 2016

(86) PCT No.: PCT/US2016/023924
§ 371 (c)(1),
(2) Date: Oct. 19, 2017

(87) PCT Pub. No.: WO2016/176946
PCT Pub. Date: Nov. 3, 2016

(65) Prior Publication Data
US 2018/0117976 A1 May 3, 2018

Related U.S. Application Data

(63) Continuation of application No. PCT/US2015/028211, filed on Apr. 29, 2015.

(51) Int. Cl.
*B60C 25/00* (2006.01)
*G01M 17/02* (2006.01)
(Continued)

(52) U.S. Cl.
CPC ............ *B60C 25/002* (2013.01); *B60C 19/00* (2013.01); *B60C 25/05* (2013.01); *G01M 17/02* (2013.01); *G01N 27/82* (2013.01); *B60C 25/005* (2013.01)

(58) Field of Classification Search
CPC .. G01M 17/02; G01M 17/021; G01M 17/022; G01M 17/027; G01M 17/025;
(Continued)

(56) References Cited

U.S. PATENT DOCUMENTS 3,967,498 A 7/1976 Pezzillo
4,475,384 A 10/1984 Christie
(Continued)

FOREIGN PATENT DOCUMENTS

EP 1037753 B1 9/2000
EP 1245948 A1 10/2002
(Continued)

OTHER PUBLICATIONS

International Search Report dated Apr. 29, 2015 for PCT/US2015/010154.
(Continued)

*Primary Examiner* — Andre J Allen
(74) *Attorney, Agent, or Firm* — Dority & Manning, P.A.

(57) ABSTRACT

A sensor device for tire inspection is provided. The sensor device is configured for removable placement upon or near the surface of the tire. The sensor device includes one or more tire inspection sensors configured to inspect e.g., the condition of one or more components or portions of the tire. The sensor device also includes one or more proximity sensors configured to detect whether the sensor device is in proper proximity of the tire such that the one or more tire inspection sensors can operate correctly.

18 Claims, 5 Drawing Sheets

(51) Int. Cl.
*B60C 19/00* (2006.01)
*B60C 25/05* (2006.01)
*G01N 27/82* (2006.01)

(58) Field of Classification Search
CPC ...... G01M 17/024; G01M 17/10; G01M 7/08;
G01M 17/0076; G01M 17/013; G01M
17/03; G01M 17/04; G01M 17/06; G01M
17/08; G01M 1/02; G01M 1/045; G01M
1/12; G01M 1/225; G01M 3/04; G01M
3/40; G01M 5/0091; G01M 7/02; G01M
99/00; G01M 99/002; B60C 23/0494;
B60C 23/04; B60C 23/0493; B60C
2019/004; B60C 19/00; B60C 23/0498;
B60C 23/064; B60C 23/0488; B60C
23/0496; B60C 23/0408; B60C 23/041;
B60C 23/0411; B60C 23/20; B60C
11/243; B60C 11/246; B60C 23/06; B60C
23/061; B60C 23/00; B60C 23/0486;
B60C 11/0083; B60C 13/003; B60C
2009/2038; B60C 23/003; B60C 23/004;
B60C 23/02; B60C 23/0401; B60C
23/0406; B60C 23/0416; B60C 23/0433;
B60C 23/0455; B60C 23/0489; B60C
23/0491; B60C 25/002; B60C 25/005;
B60C 25/007; B60C 29/02; B60C 3/04;
B60C 99/00; B60C 99/006; B60C 11/24;
B60C 13/001; B60C 13/02; B60C
15/0036; B60C 17/02; B60C 2009/0071;
B60C 2009/2022; B60C 2200/02; B60C
2200/06; B60C 2200/065; B60C 23/001;
B60C 23/007; B60C 23/008; B60C
23/0413; B60C 23/0427; B60C 23/0447;
B60C 23/0454; B60C 23/0459; B60C
23/0467; B60C 23/0471; B60C 23/0472;
B60C 23/0474; B60C 23/0476; B60C
23/0484; B60C 23/065; B60C 23/066;
B60C 23/10; B60C 25/0548; B60C
25/056; B60C 25/132; B60C 25/138;
B60C 25/18; B60C 29/005; B60C 9/005;
B60C 9/18; B60C 9/1807; B60C 9/22;
B60C 9/28
USPC .................................................. 73/146–146.8
See application file for complete search history.

(56) References Cited

U.S. PATENT DOCUMENTS

| | | | |
|---|---|---|---|
| 4,520,307 A | 5/1985 | Weiss | |
| 5,557,256 A | 9/1996 | Achterholt | |
| 6,304,090 B1 | 10/2001 | Weiss | |
| 6,832,513 B2 | 12/2004 | Weiss | |
| 6,907,777 B2 | 6/2005 | Weiss | |
| 7,826,192 B2 | 11/2010 | Sinnett et al. | |
| 9,927,326 B2 | 3/2018 | Schober | |
| 9,976,937 B2 | 5/2018 | Charlat et al. | |
| 10,006,835 B2 | 6/2018 | Schober et al. | |
| 10,060,832 B2 | 8/2018 | Schober et al. | |
| 2004/0016293 A1 | 1/2004 | Weiss | |
| 2006/0028203 A1 | 2/2006 | Kawashima | |
| 2006/0170420 A1 | 8/2006 | Nishimizu | |
| 2007/0028679 A1 | 2/2007 | Stoila et al. | |
| 2007/0279203 A1* | 12/2007 | Thomas | B60C 23/068 340/447 |
| 2008/0168833 A1 | 7/2008 | Awad | |
| 2008/0216567 A1* | 9/2008 | Breed | B60C 11/24 73/146.5 |
| 2008/0300801 A1 | 12/2008 | Miyoshi | |
| 2009/0009162 A1 | 1/2009 | Nishimizu | |
| 2010/0276044 A1 | 11/2010 | Heise et al. | |
| 2012/0038357 A1 | 2/2012 | Brandon | |
| 2012/0112898 A1 | 5/2012 | Yu et al. | |
| 2012/0137761 A1 | 6/2012 | Dardelin | |
| 2013/0131915 A1 | 5/2013 | Masago | |
| 2013/0162265 A1 | 6/2013 | Beccavin et al. | |
| 2014/0070935 A1 | 3/2014 | Wang | |
| 2015/0191057 A1* | 7/2015 | Schober | G01M 17/02 73/146 |
| 2016/0349149 A1* | 12/2016 | Schober | G01R 33/072 |
| 2016/0377507 A1* | 12/2016 | Schober | G01M 17/02 73/146 |
| 2017/0227496 A1 | 8/2017 | Judd et al. | |

FOREIGN PATENT DOCUMENTS

| | | |
|---|---|---|
| EP | 1349249 A1 | 10/2003 |
| WO | WO2012/036674 A1 | 3/2012 |
| WO | WO2014/077846 | 5/2014 |

OTHER PUBLICATIONS

International Search Report dated Apr. 28, 2015 for PCT/US2015/010159.

International Search Report dated Mar. 31, 2016 for PCT/US2016/012116.

International Search Report dated Jul. 31, 2015 for PCT/US15/28211.

International Search Report dated Aug. 11, 2016 for PCT/US2016/23924.

International Search Report dated Mar. 23, 2016 for PCT/US2016/012119.

* cited by examiner

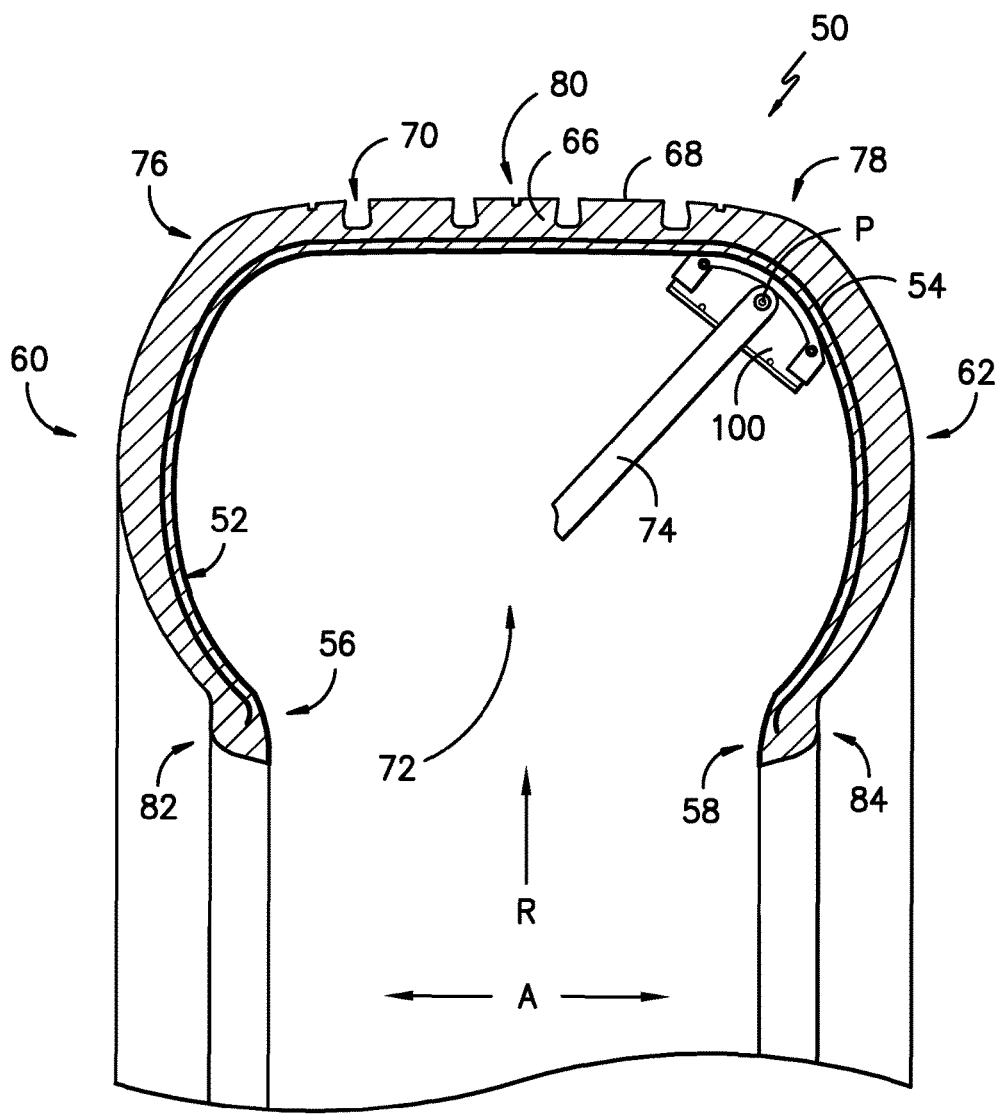
FIG. -1-

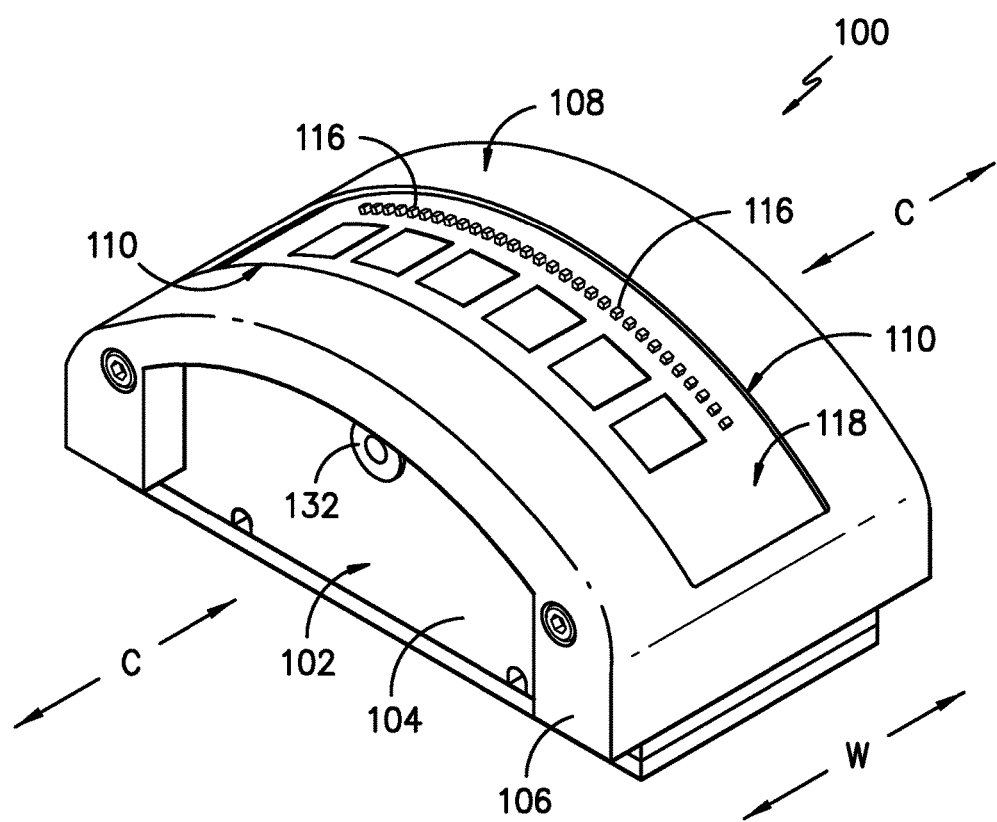
FIG. -2-

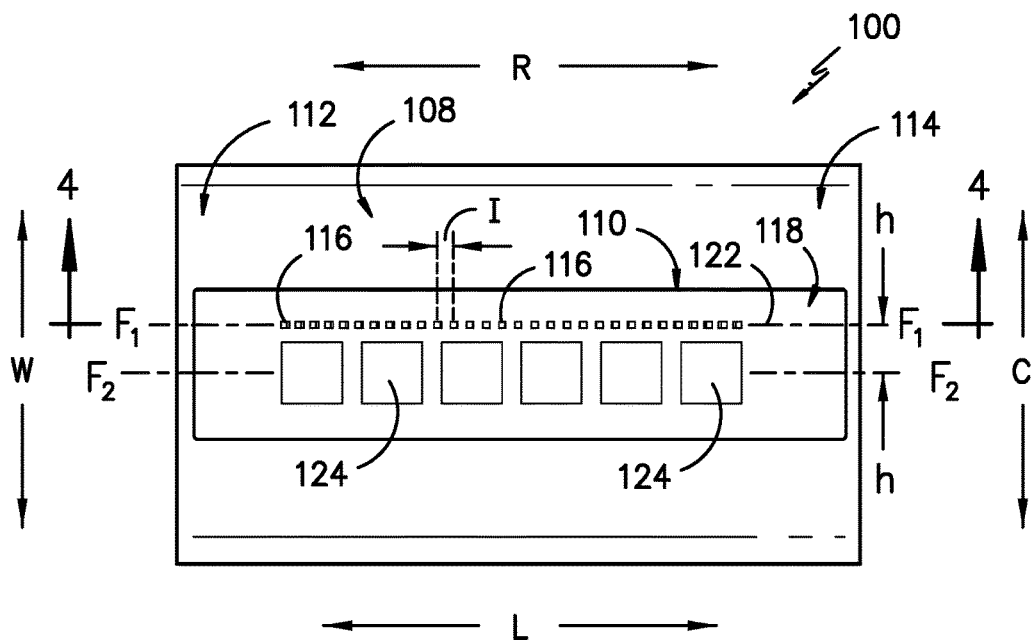
FIG. -3-
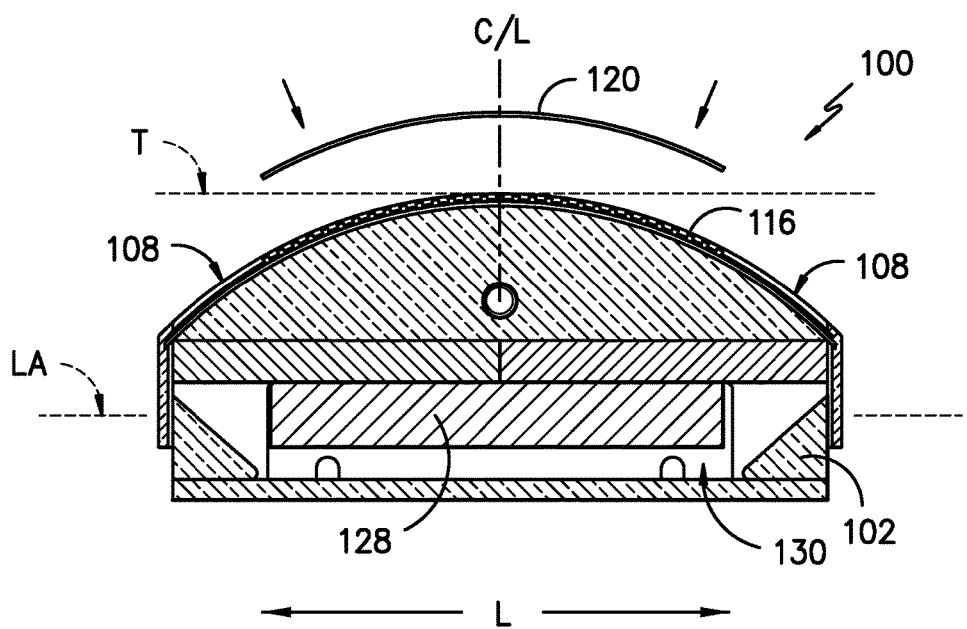
FIG. -4-

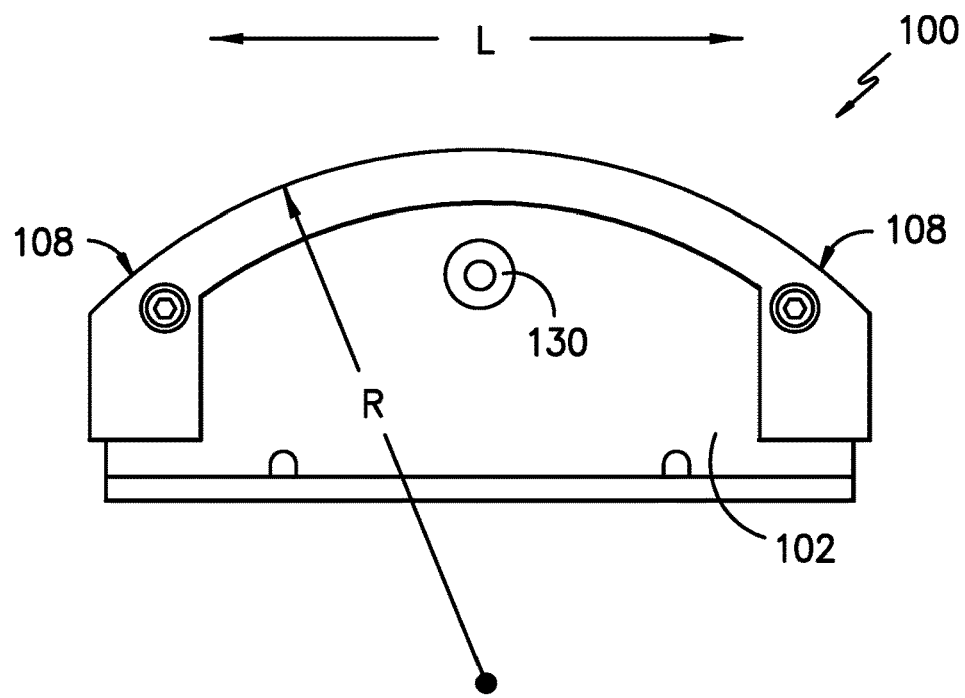
FIG. -5-
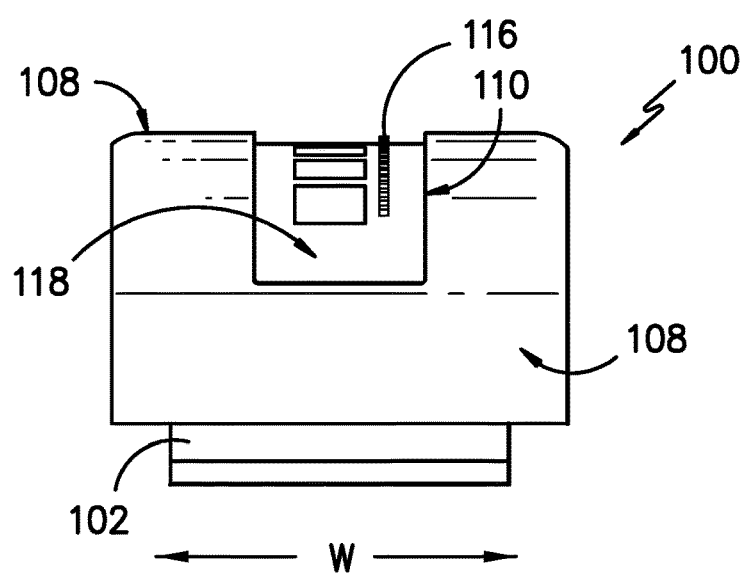
FIG. -6-

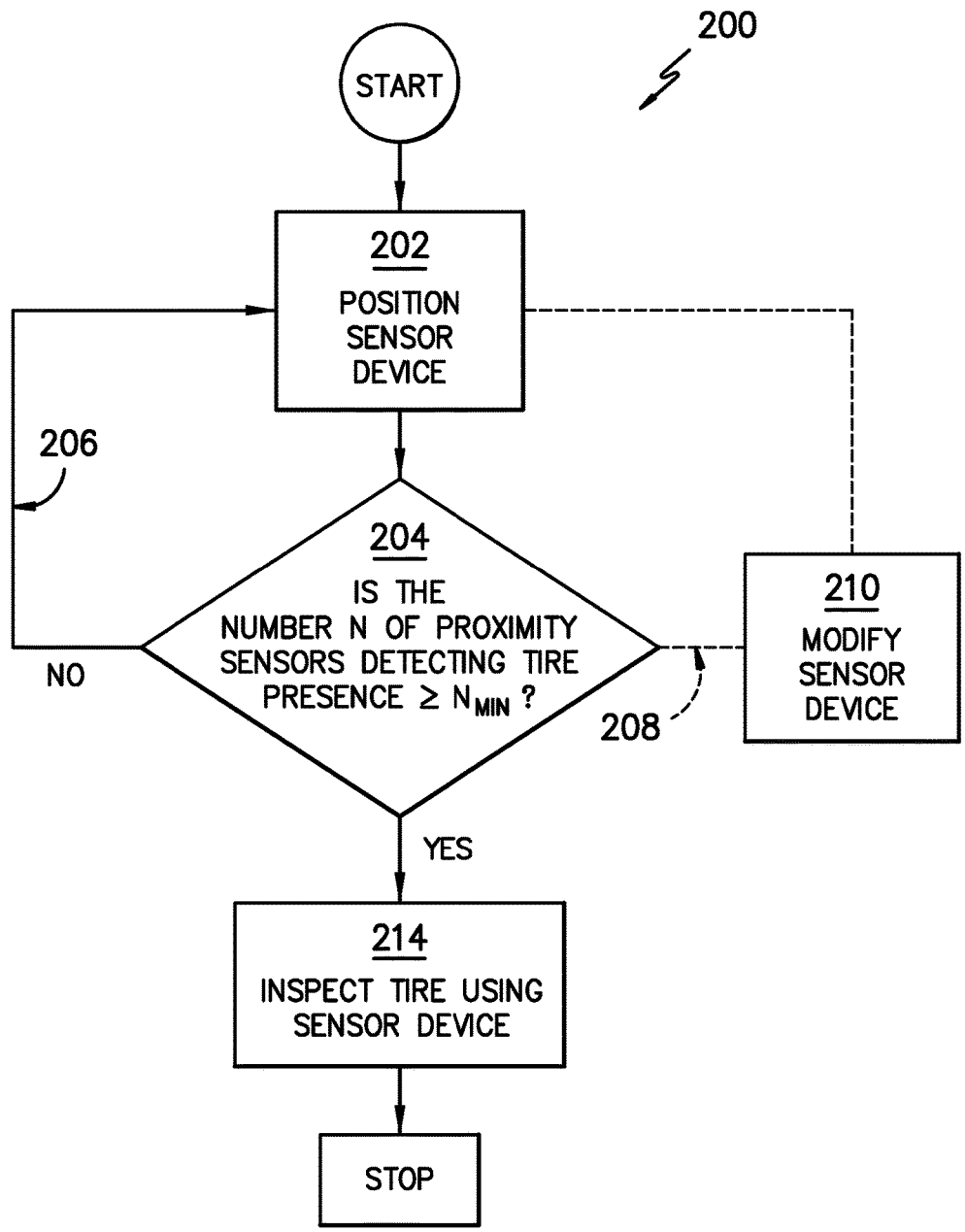
FIG. -7-

SENSING DEVICE WITH PROXIMITY DETECTION FOR TIRE INSPECTION

PRIORITY STATEMENT

The present application claims priority to International Application PCT/US15/28211, filed Apr. 29, 2015 in the United States Receiving Office.

FIELD OF THE INVENTION

The subject matter of the present disclosure relates generally to a sensing device for inspecting a tire that can also detect whether the device is within proper proximity of one or more sensors used to inspect the tire.

BACKGROUND OF THE INVENTION

The inspection of a new or worn tire can be useful for investigating one or more aspects of its condition. Such an inspection may explore e.g., surface features of the tire or internal features that are normally hidden from view. Frequently, conducting the inspection without damaging or deconstructing the tire is desirable. Where internal features are to be inspected, the use of one or more specially designed devices is typically necessary.

By way of example, a known tire construction uses a body ply having reinforcement elements that extend from bead portion to bead portion through opposing sidewall portions, and a crown portion of the tire. Sometimes referred to as the carcass ply or reinforcing ply, the body ply is typically anchored at the beads and maintains the overall shape of the tire as the tire is inflated and used. The reinforcement elements of the body ply are usually oriented substantially along the radial direction (a direction perpendicular to the axis of rotation) and can include e.g., a ferrous metal.

During use of the tire, these reinforcement elements (sometimes referred to as cords) may be damaged e.g., from impact with objects in the roadway, travel over curbs, and other damaging events. Fatigue of the reinforcement elements as result of continued use at high loads and/or low air pressure can also occur. In some situations, the reinforcement elements may be completely broken as a result of such events. Unfortunately, this damage may not be readily discoverable from a visual inspection of the exterior of the tire because the reinforcement elements are contained within the rubber materials used to construct the tire.

Commercial tires are commonly reused after a process referred to as retreading. With retreading, worn tread is removed from the tire and a new tread belt or tread section is installed onto the tire. Replacement of the tread is less expensive than replacing the whole tire and allows additional mileage to be obtained using the same tire carcass. This practice is common particularly with commercial tires for heavy trucks. Before replacing the tread, however, it is advantageous to inspect the tire, including the internal reinforcement elements of the body ply, for damage or wear. In certain situations, inspection may reveal that replacement of the tire is required rather than retreading. Alternatively, repair of the tire may be required. By way of example, specially designed optical instruments may be used to inspect external or surface features. However, as stated above, not all damage to interior elements such as e.g., the reinforcement elements of the body ply are readily apparent from a visual inspection alone.

Whether investigating external features or internal features such as e.g., the reinforcement elements, automation of the tire inspection process is very desirable so that multiple tires may be inspected economically and expediently. Challenges face such automation because tires come in a variety of shapes and sizes. More specifically, the profile, height, and width (along the axial direction) can vary substantially from tire to tire. For tire inspection, some sensors require placement at close proximity to the surface of the tire. For example, placement of one or more sensors near an inner surface of the tire either in contact with the tire or in close proximity thereto may be required. Automating such a process can be problematic with tire profile and size changes from tire to tire.

Furthermore, increased complexities can be encountered in the detection of discontinuities at certain locations of the tire. The repeatable and proper placement of such sensors along e.g., the shoulder portion of the tire at the inner surface can be particularly challenging because of the curvature at the shoulder portion and the variability of the curvature between tires of different sizes and types. Similarly, repeatable and proper placement of such sensors near the bead portion can also be challenging.

Accordingly, a device that can be repeatably and properly positioned for tire inspection would be useful. More particularly, a device for tire inspection that can be placed near or in contact with the surface of the tire and at different locations would be beneficial. Such a device that can detect whether it is in proper proximity relative to the tire or a surface of the tire such that one or more tire inspections sensors can properly operate would also be useful. Such a device that can be repeatably and properly positioned for the inspection of multiple tires having different sizes or profiles would be particularly beneficial.

SUMMARY OF THE INVENTION

The present invention provides a sensor device for tire inspection. The sensor device is configured for removable placement upon or near the surface of the tire. The sensor device includes one or more tire inspection sensors configured to inspect e.g., the condition of one or more components or portions of the tire. The sensor device also includes one or more proximity sensors configured to detect whether the sensor device is in proper proximity of the tire such that the one or more tire inspection sensors can operate correctly. Additional objects and advantages of the invention will be set forth in part in the following description, or may be apparent from the description, or may be learned through practice of the invention.

In one exemplary embodiment, the present invention provides a sensor device for tire inspection that is removably positionable along an inner surface of a tire. The tire defines radial, axial, and circumferential directions. The sensor device includes a body having an outermost inspection surface configured for placement along a surface of the tire. A plurality of tire inspection sensors are positioned at the outermost inspection surface. The tire inspection sensors are displaced from each other along the radial direction of the tire when the device is positioned along the surface of the tire or a component within the tire.

A plurality of tire proximity sensors are positioned at the outermost inspect surface of the device. The tire proximity sensors are displaced from each other along the radial direction of the tire when the device is positioned along the surface of the tire or a component within the tire. Each tire proximity sensor is configured to provide a signal indicative of the distance between the tire proximity sensor and the surface of the tire or a component within the tire.

In another exemplary aspect, the present invention provides a method for inspecting a tire using a sensor device. The sensor device includes a plurality of tire inspection sensors and a plurality of tire proximity sensors spaced apart along a radial direction of the tire when the sensor device is positioned adjacent to the tire. This exemplary method includes positioning the sensor device adjacent to a surface of the tire; determining whether at least a predetermined number, $N_{MIN}$, of a total number, $N_{TOT}$, of tire proximity sensors are detecting the presence of the tire and, if not, then repositioning the sensor device adjacent to the surface of the tire, and repeating the determining.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a cross-sectional view of a portion of an exemplary tire as well as a side view of an exemplary embodiment of the present invention.

FIG. 2 illustrates a perspective view of an exemplary embodiment of the present invention.

FIG. 3 provides a top view of the exemplary embodiment of FIG. 2.

FIG. 4 is a cross-sectional view along lines 4-4 of the exemplary embodiment in FIG. 3.

FIG. 5 is a side view of the exemplary embodiment of FIG. 2.

FIG. 6 is an end view of the exemplary embodiment of FIG. 2.

FIG. 7 provides a flow chart illustrating an exemplary method of the present invention.

DETAILED DESCRIPTION

For purposes of describing the invention, reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

"Meridian plane" is a plane within which lies the axis of rotation of the tire. FIG. 1 is a cross-section of an exemplary tire 50 taken along a meridian plane.

The "crown portion" of the tire is the portion that extends along the axial direction A (which is the direction parallel to the axis of rotation of the tire) between the sidewall portions of the tire including the tread and components positioned radially inward of the tread.

"Body ply" or "carcass" or "carcass ply" is a ply that extends between and from the bead portions on opposing sides of the tire, through the opposing sidewall portions, and across the crown portion of the tire. The body ply may include ferrous reinforcements.

The "radial direction" is perpendicular to the axis of rotation of the tire and is denoted in the figures with an "R" and a directional arrow. The axial direction, parallel to the axis of rotation, is denoted in the figures with an "A" and directional arrows.

The "circumferential direction" of the tire (also referred to as the longitudinal direction of the tire) is the direction corresponding to the periphery of the tire and is defined by the direction of rotation of the tire during normal operation. The circumferential direction is denoted in the figures with a C and directional arrows.

In the description that follows, directions R, A, and C are denoted in drawings of the exemplary embodiments to denote the orientation of the embodiments relative to the tire when the sensor device is positioned for tire inspection. Additionally, the positions of various components of exemplary embodiments may be described with reference to these directions as determined relative to sensor device 100 when it is positioned for tire inspection.

FIG. 1 illustrates a cross-sectional view of an exemplary tire 50 along a meridian plane. A side view of an exemplary embodiment of a sensor device 100 of the present invention is shown. Sensor device 100 is removably positioned at an inner surface 52 of tire 50 for purposes of tire inspection. The construction of tire 50 includes a body ply 54 that extends from bead portions 56 and 58, through opposing sidewall portions 60 and 62, through opposing shoulder portions 76 and 78, and through crown portion 80 with tread portion 66. Tread portion 66 is positioned radially outward of body ply 54. For exemplary tire 50, tread portion 66 includes ribs 68 defined by grooves 70.

In this exemplary embodiment, sensor device 100 is removably positioned within the interior 72 of tire 50 along inner surface 52 by a positioning system that includes a support arm 74. Sensor device 100 is pivotally connected to support arm 74 at point P, which allows the orientation of device 100 to be adjusted to more readily match the profile of the inner surface 52 of tire 50. Support arm 74 can be connected at point of attachment 132 (FIG. 2) and is provided by way of example only. Other positioning systems may be used with sensor device 100 as well.

Certain embodiments of the sensor device of the present invention, as described herein, are particularly suited for use along the inner surface of the shoulder portion of a variety of tire sizes of different widths and profiles. For example, the particular embodiment of sensor device 100 shown in FIG. 1 is positioned along a shoulder portion 76 of tire 100. While the present invention is not limited to use along a shoulder portion 76, this particular embodiment of sensor device 100 has a shape that is conducive to use along the shoulder portions of tire 50 as will be further described. In other embodiments of the invention, a sensor device may be provided having a shape more useful for positioning at other locations of the tire. For example, the sensor device may be of a shape or configuration more suited for tire inspection at either of the opposing bead portions 82 and 84 of tire 50. The sensor device may be configured for inspection at other locations of tire 50 as well.

During inspection, sensor device 100 may be placed very close (e.g., within 5 mm to 6 mm) of a surface of the tire such as e.g., inner surface 52. Sensor device 100 may even contact surface 52 as shown in FIG. 1. Once positioned, tire 50 can be rotated about its axis of rotation so as to scan or detect the tire at this radial position of the tire surface along a complete circumference of tire 50. For example, sensor device 100 may be placed as shown in order to detect broken reinforcement elements (not shown) of body ply 54 over a complete circumference of tire 50. As will be further described, sensor device 100 allows the placement of one or more tire inspection sensors in close proximity to inner surface 52, which may be necessary for proper testing, and also expedites testing by allowing a complete inspection from a single rotation of tire 50. Additionally, sensor device 100 includes one or more tire proximity sensors that can be used to detect whether sensor device 100 is within an appropriate proximity (i.e. distance) of tire 50 such that a proper detection or scan can be performed using the tire inspection sensors.

Referring now to FIG. 2, sensor device 100 includes a body 102 that may be constructed from e.g., an inner portion 104 and an outer portion 106. Body 102 includes an outermost inspection surface 108. As used herein, "outermost" means that the inspection surface 108 is the closest part of body 102 to that portion of the surface of tire 50 that is being inspected. For the example of FIG. 1, such surface would be inner surface 52. In other embodiments of the invention, other surfaces may be targeted for inspection.

Referring now to all FIGS. 2 through 6, body 102 defines a longitudinal direction L of body 52 and width direction W that is orthogonal to direction L of body 52. When body 102 is placed along the inner surface 52 of tire 50, body 102 is oriented such that the longitudinal direction L of body 52 is orthogonal to the circumferential direction C of tire 50 (FIGS. 2 and 3). In this orientation, the width direction W of body 102 would be parallel to circumferential direction C of tire 50 and orthogonal to radial direction R.

For this exemplary embodiment, body 102 includes an aperture 110 defined by outermost inspection surface 108. Aperture 110 extends longitudinally along direction L between a first end 112 and a second end 114 of outermost inspection surface 108 (FIG. 3). Sensor device 100 can be equipped with a protective cap 120 (FIG. 4) for protection of one or more sensors positioned at the outermost inspection surface 108—particularly during rotation of the tire past device 100. Alternatively, outermost inspection surface 108 can be provided without aperture 110 and/or cap 120. For example, sensors may be positioned on or beneath outermost inspection surface 108 in other exemplary embodiments of the invention.

Referring to FIGS. 2 and 3, sensor device 100 includes a plurality of tire inspection sensors 116 that are displaced from each other along the longitudinal direction L of body 102. During a tire inspection, longitudinal direction L of body 102 is oriented substantially (e.g., within ±5 degrees) along radial direction R of tire 50 when sensor device 100 is properly positioned. As used herein, "tire inspection sensor" refers to a sensor that can detect or measure one or more structural, physical, or chemical properties or conditions of tire 50. By way of example, sensors 116 may include Hall Effect sensors, strain gauge sensors, temperature sensors, optical sensors, and/or other type sensors as well. Combinations of different sensors may also be used. While only one tire inspection sensor 116 may be used, certain sensor types may require the use of multiple sensors for proper detection or measurement.

For the exemplary embodiment of sensor device 100 shown in the figures, sensors 116 are provided as a plurality of Hall Effect sensors that are capable of detecting breaks in the ferrous reinforcement elements of body ply 54. Hall Effect sensors 116 provide a signal indicative of the presence of magnetic flux as well as the magnetic flux density and, therefore, can be used to detect changes in magnetic flux density. In one embodiment of the invention, thirty-two Hall Effect sensors 116 are used and are positioned at intervals I of about 2.5 mm (see, e.g., FIG. 3). For detecting breaks in the reinforcements of body ply 54, the use of multiple Hall Effect sensors 116 improves the effectiveness of the sensor device 100 in detecting breaks. More particularly, shoulder portions 76 and 78 of tire 50 are high flexion zones and, therefore, present a location where breaks in the reinforcements of body ply 54 are likely to be found. The use of multiple sensors 116 ensures at least one sensor 116 will be located on each side of a break in a shoulder portion 76 or 78 as tire 50 is rotated during the inspection process.

Tire inspection sensors 116 are positioned adjacent to each other and arranged linearly along a first row 122 defining a first axis F1. While only one row 122 of tire inspection sensors 116 is shown, multiple rows of tire inspections sensors may be used. Such rows may be parallel to each other or positioned at an angle with respect to one another. Additionally, in other embodiments of the invention, sensors 116 may be positioned in other, non-linear configurations on body 102.

Sensor device 100 also includes a plurality of tire proximity sensors 124 that are displaced from each other along the longitudinal direction L of body 102. As used herein, "tire proximity sensor" refers to a sensor that can detect whether body 102 is within a certain distance or proximity to tire 50 (e.g., a surface of the tire of a component thereof). For example, tire proximity sensors 124 can determine whether body 102 of device 100 is within a certain range of distance between sensor support surface 118 and an inner surface 52 such that tire inspection sensors 116 can properly detect breaks in the reinforcing elements of body ply 54. The proximity required may vary depending upon e.g., the type, range, and sensitivity of sensors 116. For example, in some embodiments, contact between outermost inspection surface 108 and inner surface 52 of tire 50 may be required. In other embodiments, a distance between outermost inspection surface 108 and inner surface 52 of about 5 mm or less may be acceptable. By way of example, tire proximity sensors 124 may include capacitive sensors. Other proximity sensor types may be used as well.

Tire proximity sensors 124 are positioned adjacent to each other and arranged linearly along a second row 126 defining a second axis $F_2$. While only one row 126 of tire proximity sensors 126 is shown, multiple rows of tire proximity sensors may be used. Such rows may be parallel to each other or positioned at an angle with respect to one another. Additionally, in other embodiments of the invention, sensors 126 may be positioned in other, non-linear configurations on body 102.

As shown in FIG. 3, first axis $F_1$ and second axis $F_2$ are separated by a predetermined distance h. While first axis $F_1$ and second axis $F_2$ may be coincident, generally a certain non-zero value for distance h will be required depending e.g., the types of sensors 116 and 124 that are employed and the size of the sensors. Also, first axis $F_1$ and second axis $F_2$ may be oriented at a non-zero angle $\alpha$ with respect to each other. Angle $\alpha$ may be, for example, in the range of 0 degrees $< \alpha \leq 4$ degrees. In still another embodiment, angle $\alpha$ may be about 1 degrees. Other angles may be used as well. The use of a non-zero angle $\alpha$ between first axis $F_1$ and second axis $F_2$ may allow sensors 116 and 124 to more closely match the radial angle of reinforcements within the tire.

For this exemplary embodiment, sensors 116 and 124 are positioned within aperture 110 and are surrounded by outermost inspection surface 108. Sensors 116 and 124 are supported upon a sensor support surface 118 (which may e.g., a printed circuit board or other substrate) that may be slightly recessed or positioned inwardly relative to outermost inspection surface 108. As shown, sensor support surface 118 is parallel to the outermost inspection surface 108. More particularly, sensor support surface 118 has a curvature or profile along the longitudinal direction L that matches the profile of outermost inspection surface 108.

Referring now to FIGS. 1, 4, and 5, outermost inspection surface 108 has a particular profile along the longitudinal-direction L of body 102 as shown in these figures. More particularly, when sensor device 100 is placed against inner surface of tire 50 (as in FIG. 1), outermost inspection surface 108 has a profile of an arc of a circle. The arc of this circle has a radius R (FIG. 5) that is orthogonal to the circumferential direction C of tire 50 when sensor device 100 is positioned against inner surface 52 as shown in FIG. 1. The profile of outermost inspection surface 108 along its width (W) is substantially flat (FIG. 6).

For the exemplary embodiments of FIGS. 1 through 6, the inventors have discovered that the profile for the outermost inspection surface 108 sufficiently matches the shape of the inner surface of most tires along the shoulder zone when radius R (FIG. 5) is in the range of 50 mm to 75 mm. This allows sensor device 100 to be used over a wide variety of tire shapes and sizes. More particularly, this profile allows the placement of sensors 116 in close proximity to inner surface 52 so that tire 50 can be properly inspected by a single rotation of tire 50 past sensor device 100.

In one exemplary embodiment, the inventors have determined that when radius R is about 74 mm, the profile of the outermost inspection surface 108 conforms to a commensurate inner surface shape of approximately 85 percent of commercially available heavy truck/commercial truck tire profiles. In another exemplary embodiment, the inventors have determined that when radius R is about 52 mm, the profile of the outermost inspection surface 108 conforms to commensurate inner surface shape of other commercially available heavy truck/commercial truck tire profiles. Accordingly, sensor device 100 can be provided with multiple bodies 102 each having a different radius of curvature that can be substituted for one another depending upon which best matches the profile of the tire being inspected. As previously indicated, where sensor device 100 is being used to inspect other locations of tire 50 than sidewall portions 60 or 62, different shapes for body 102 and/or outermost inspection surface 108 may be used. For example, a U-shape or L-shape for body 102 and/or outermost inspection surface 108 may be used for inspecting bead portions 82 and 84.

As shown in FIG. 4, when sensors 116 are Hall Effect sensors, device 100 can be equipped with a permanent magnet 128 in order to create fields of magnetic flux used in detecting breaks in ferrous reinforcements. As shown, body 102 defines a compartment 130 into which magnet 128 is received. For this exemplary embodiment, magnet 128 is oriented with a longitudinal axis LA that is parallel to a line T that is tangent to outermost detection surface 108 at the centerline C/L of device 100. This orientation ensures a specific field of magnetic flux is created relative to the plurality of sensors 116. More than one magnet and/or magnet type may be used as well.

An exemplary method for inspecting a tire using a sensor device will now be described with reference of FIG. 7. Using the teachings disclosed herein, one of skill in the art will understand that such exemplary method is provided by way of example only and other methods may be employed including e.g., variations in the order of steps or using additional steps. Also, the method will be described with reference to the sensor device 100 of FIGS. 1 through 6 with an understanding that sensor devices of other shapes and configurations may be employed as well.

Referring to FIG. 7 and starting with step 202, in one exemplary method, sensor device 100 is positioned adjacent to the surface of a tire such as the inner surface 52 of tire 50. After placement, in step 204, a determination is made regarding whether sensor device 100 is within the proper proximity to the surface of tire 50 such that tire inspection sensors 116 can properly function to detect, scan, or measure one or more properties or aspects of tire 50. When tire proximity sensors 124 are placed within the proper proximity or distance of tire 50, a number N of sensors 124 provide a signal that can be received by e.g., a controller or other computing device. As such, the controller can determine whether the number N of proximity sensors detecting the presence of the tire exceeds a certain minimum predetermined value, $N_{MIN}$, of the total number, $N_{TOT}$, of tire proximity sensors 124 such that the controller can proceed to process signals produced by tire inspection sensors 116.

For example, assuming the total number, $N_{TOT}$, of tire proximity sensors 124 is six. Based on e.g., the type, number, and sensitivity of tire inspection sensors 116, it may be determined that the minimum number, $N_{MIN}$, of tire proximity sensors 124 that should detect the presence of tire 50 must be at least three. Such may be the minimum number, $N_{MIN}$, determined as necessary for enough tire inspection sensors 116 to be able to operate properly and reliably—i.e. provide an accurate inspection of tire 50.

One sensor device 100 has been positioned, depending upon the shape of tire 50 and the placement of body 102 relative to the inner surface 52 of tire 50, all six proximity sensors 124 may provide a signal indicating that sensor device 100 (more importantly—the tire inspection sensors 116) is within the proper proximity. However, if e.g., only two proximity sensors 124 are providing a signal indicating sensor device 100 is within the proper proximity, it may be determined that the inspection cannot proceed because e.g., tire inspection sensors 116 will not be able to properly inspect tire 100 or such an inspection would unreliable. By way of example, the signal from proximity sensors 120 may be binary or may provide a voltage output that must exceed a certain predetermined level to be considered a positive indication of the proper proximity to tire 50. Other signal types may also be used.

As indicated by line 206, in the event the predetermined number, $N_{MIN}$, or more of the total number, $N_{TOT}$, of tire proximity sensors are not detecting the presence of the tire, then step 202 is repeated such that sensor device 100 is repositioned. For example, support arm 74 may be moved and/or sensor device 100 may be rotated about pivot point P so as reposition the outermost inspection surface 108 relative to the inner surface 52 of tire 50. The purpose of such repositioning is to relocate tire inspection sensors 116 in closer proximity. At a time simultaneous with, or after, such repositioning, step 204 is repeated such that another determination is as to whether at least the predetermined number, $N_{MIN}$, of the total number, $N_{TOT}$, of tire proximity sensors 124 are providing a signal indicating that the tire is within the proper proximity. If not, in one exemplary aspect of the invention, sensor device 100 can be repositioned until at least the predetermined number, $N_{MIN}$, of the tire proximity sensors are provided the desired signal.

Alternatively, in another exemplary aspect of the present invention, such repositioning can be attempted a predetermined number of times, $N_{REP}$, or for a predetermined time period. If the desired signal from at least the predetermined number, $N_{MIN}$, of tire proximity sensors 124 cannot be obtained by repositioning, then in step 210 the sensor device 210 is modified. Such modification could include e.g., changing the body 102 to provide a different shape for sensor device 100. For example, a body 102 having a different radius of curvature for the outermost inspection surface could be used. If changing the body 102 does not allow for the proper placement of sensor device 100, it may be concluded that other problems exist.

Once the minimum number, $N_{MIN}$, of proximity sensors 124 provide signals indicating sensor device 100 is within proper proximity of tire 50, the controller can then reliably process the signals receiving the tire inspection sensors 116 as in step 214.

As used herein, the term "method" or "process" refers to one or more steps that may be performed in other ordering than shown without departing from the scope of the presently disclosed invention. As used herein, the term "method" or "process" may include one or more steps performed at least by one electronic or computer-based apparatus. Any sequence of steps is exemplary and is not intended to limit methods described herein to any particular sequence, nor is it intended to preclude adding steps, omitting steps, repeating steps, or performing steps simultaneously. As used herein, the term "method" or "process" may include one or more steps performed at least by one electronic or computer-based apparatus having a processor for executing instructions that carry out the steps.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A sensor device for tire inspection that is removably positionable along an inner surface of a tire, the tire defining radial, axial, and circumferential directions, the device comprising:
    a body comprising an outermost inspection surface configured for removable positioning along a surface of the tire;
    a plurality of tire inspection sensors positioned at the outermost inspection surface, the tire inspection sensors displaced from each other along the radial direction of the tire when the device is positioned along the surface of the tire; and
    a plurality of tire proximity sensors positioned at the outermost inspection surface of the device, the tire proximity sensors displaced from each other along the radial direction of the tire when the device is positioned along the surface of the tire, each tire proximity sensor configured to provide a signal indicative of the distance between the tire proximity sensor and the surface of the tire or a component within the tire.

2. The sensor device of claim 1, wherein the tire proximity sensors are arranged linearly along a row.

3. The sensor device of claim 1, wherein the tire proximity sensors are positioned adjacent to the tire inspection sensors.

4. The sensor device of claim 1, wherein each tire proximity sensor comprises a capacitive sensor.

5. The sensor device of claim 1, wherein each tire inspection sensor comprises a Hall Effect sensor.

6. The sensor device of claim 5, further comprising a magnet received within a compartment defined by the body.

7. The sensor device of claim 6, wherein the outermost inspection surface of the sensor device has a profile defined by the arc of a circle, and wherein the magnet extends linearly along a direction that is parallel to a line tangent to a center of the arc of the circle.

8. The sensor device of claim 1, wherein the body defines a longitudinal direction extending orthogonal to the circumferential direction of the tire when positioned along the surface, and wherein the outermost inspection surface defines an aperture in which the tire inspection sensors and tire proximity sensors are received.

9. The sensor device of claim 1, wherein the outermost inspection surface has a profile of an arc of a circle with a radius of curvature that is orthogonal to the circumferential direction of the tire when positioned along the surface.

10. The sensor device of claim 9, wherein the radius of curvature of the outermost inspection surface is in the range of 50 mm to 75 mm.

11. A method for inspecting a tire using a sensor device, the sensor device comprising a plurality of tire inspection sensors and a plurality of tire proximity sensors spaced apart along a radial direction of the tire when the sensor device is positioned adjacent to the tire, the method comprising:
    positioning the sensor device adjacent to a surface of the tire,
    determining whether at least a predetermined number, $N_{MIN}$, of a total number, $N_{TOT}$, of tire proximity sensors are detecting the presence of the tire and, if not, then repositioning the sensor device adjacent to the surface of the tire, and
    repeating the determining.

12. The method for inspecting a tire as in claim 11, wherein the determining is repeated until at least $N_{MIN}$ of the total number, $N_{TOT}$, of tire proximity sensors are detecting the presence of the tire.

13. The method for inspecting a tire as in claim 11, wherein the determining is repeated for either i) a predetermined number of times, $N_{REP}$ or ii) until at least $N_{MIN}$ of the total number, $N_{TOT}$, of tire proximity sensors are detecting the presence of the tire, whichever occurs first.

14. The method for inspecting a tire as in claim 13, wherein the sensor device includes a body having a predetermined shape based on a portion of the tire that is being inspected, and further comprising changing the predetermined shape of the body if at least $N_{MIN}$ of the total number, $N_{TOT}$, of tire proximity sensors are not detecting the presence of the tire after repositioning the sensor device for the number of predetermined times, $N_{REP}$.

15. The method for inspecting a tire as in claim 14, wherein the sensor device has an outermost inspection surface having a profile of an arc of a circle with a radius of curvature that is orthogonal to the circumferential direction of the tire when positioned along an inner surface of the tire, and wherein the changing of the predetermined shape of the body comprises changing the radius of curvature.

16. The method for inspecting a tire as in claim 11, further comprising receiving signals from one or more of the plurality of tire inspection sensors.

17. The method for inspecting a tire as in claim 11, further comprising modifying the sensor device if a predetermined number, $N_{MIN}$, of the total number, $N_{TOT}$, of tire proximity sensors are unable to detect the presence of the tire.

18. The method for inspecting a tire as in claim 17, wherein the sensor device comprises a body having an outermost inspection surface of a predetermined shape, and where modifying the sensor device comprises changing the predetermined shape of the outermost inspection surface.

* * * * *